United States Patent
Kawai

(10) Patent No.: US 9,132,289 B2
(45) Date of Patent: Sep. 15, 2015

(54) TWO-LAYER SEPARATE TYPE HAIR COSMETIC COMPOSITION

(75) Inventor: Tetsuya Kawai, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 121 days.

(21) Appl. No.: 13/321,701

(22) PCT Filed: Jun. 1, 2010

(86) PCT No.: PCT/JP2010/003669
§ 371 (c)(1),
(2), (4) Date: Nov. 21, 2011

(87) PCT Pub. No.: WO2010/146784
PCT Pub. Date: Dec. 23, 2010

(65) Prior Publication Data
US 2012/0064137 A1 Mar. 15, 2012

(30) Foreign Application Priority Data

Jun. 19, 2009 (JP) .................................. 2009-146515
May 17, 2010 (JP) .................................. 2010-113333

(51) Int. Cl.
*A61Q 5/06* (2006.01)
*A61Q 5/12* (2006.01)
*A61K 8/03* (2006.01)
*A61K 8/81* (2006.01)
*A61K 8/891* (2006.01)
*A61K 8/892* (2006.01)
*A61K 8/898* (2006.01)

(52) U.S. Cl.
CPC ... *A61Q 5/12* (2013.01); *A61K 8/03* (2013.01); *A61K 8/817* (2013.01); *A61K 8/8182* (2013.01); *A61K 8/891* (2013.01); *A61K 8/892* (2013.01); *A61K 8/898* (2013.01); *A61Q 5/06* (2013.01)

(58) Field of Classification Search
None
See application file for complete search history.

(56) References Cited

U.S. PATENT DOCUMENTS

| 4,976,956 A * | 12/1990 | Noe ............................ 424/70.12 |
| 6,585,965 B1 * | 7/2003 | Carballada et al. .......... 424/70.1 |
| 6,923,954 B2 * | 8/2005 | Doi et al. .................... 424/70.19 |

FOREIGN PATENT DOCUMENTS

| CN | 1404813 A | 3/2003 |
| JP | 60-78907 A | 5/1985 |
| JP | 62 59204 | 3/1987 |
| JP | 6 279241 | 10/1994 |
| JP | 10 316539 | 12/1998 |
| JP | 11 222415 | 8/1999 |
| JP | 11 335237 | 12/1999 |
| JP | 2001 213720 | 8/2001 |
| JP | 2002 003339 | 1/2002 |
| JP | 2006-151871 A | 6/2006 |
| JP | 2006 160708 | 6/2006 |
| JP | 2009-108052 A | 5/2009 |
| WO | WO 99/66888 | 12/1999 |
| WO | 2009 004952 | 1/2009 |

OTHER PUBLICATIONS

Office Action issued Nov. 2, 2012 in Chinese Patent Application No. 201080027216.7 (with English translation).
International Search Report issued on Aug. 31, 2010 in PCT /JP10/03669 filed on Jun. 1, 2010.
Fragrance Journal, vol. 36, No. 5, May 15, 2008, p. 95 (with unedited computer generated English translation).

* cited by examiner

*Primary Examiner* — Jyothsna Venkat
(74) *Attorney, Agent, or Firm* — Oblon, McClelland, Maier & Neustadt, L.L.P.

(57) ABSTRACT

A non-aerosol two-layer separate type hair cosmetic composition containing components (A) and (B) at a mass ratio (A)/(B) of from 0.2 to 10:
(A) a silicone with a number-average degree of polymerization of from 300 to 20,000 having a number-average particle diameter of from 0.05 to 20 μm, selected from the group consisting of dimethicone, dimethiconol, and amino-modified silicone and in an amount of from 0.1 to 6 mass %
(B) a water-soluble cationic polymer with a weight-average molecular weight of from 50,000 to 1,000,000, selected from the group consisting of polyquaternium-6, polyquaternium-7, polyquaternium-16, and polyquaternium-22,
wherein the composition consists of an oil-in-water emulsion layer and an aqueous layer.

7 Claims, No Drawings

TWO-LAYER SEPARATE TYPE HAIR COSMETIC COMPOSITION

CROSS REFERENCE TO RELATED APPLICATION

This application is a 371 of PCT/JP10/003669, filed on Jun. 1, 2010, and claims priority to the following Japanese Patent Application Nos.: 2009-146515, filed on Jun. 19, 2009; and 2010-113333, filed on May 17, 2010.

FIELD OF THE INVENTION

The present invention relates to a two-layer separate type hair cosmetic composition.

BACKGROUND OF THE INVENTION

Conventionally, hair cosmetics in the form of hair water have been known, in which an oily component is incorporated for the purpose of protection of the hair, improvement of the feel for touch, etc. Since this type of hair cosmetic is excellent in that hairs are softly manageable without stickiness and give light natural finish, many kinds thereof are proposed. However, if a large amount of an oily component is to be incorporated therein for further enhancing the performance, the cosmetic should be an emulsion form with a large amount of an emulsifier, causing problems such as deteriorating the feel for touch as compared to hair water, or difficulty of keeping the storage stability, so that the amount of an oily component capable of being incorporated is inevitably limited.

As means for solving the problems of both hair water type and emulsion type hair cosmetics, a two-layer separate type hair cosmetic has been proposed. This type of hair cosmetic consists of separated two layers and can be homogenized by shaking immediately before use, and is separated again after standing still for a while. This hair cosmetic provides a beautiful appearance, as well as an improvement of performances due to the capability of incorporating oily components in a large amount.

The two-layer separate type hair cosmetics are further classified into mainly the below two types:

1) Two-layer separate type, consisting of oil layer/aqueous layer (for example, Patent Documents 1 and 2), and
2) Two-layer separate type, consisting of emulsion layer/aqueous layer (for example, Patent Documents 3 and 4).

In the case of the oil layer/aqueous layer type of 1), when only an oil layer and an aqueous layer are simply used in combination, the two layers are mechanically dispersed, however immediately separated even by shaking immediately before use, and application thereof in a homogeneous form to the hair is thus difficult. By use of an emulsifier, it is possible to mix and emulsify homogeneously these layers while shaking, and to maintain the emulsified form, however in this case, a difficulty of the emulsion to be separated when being left standing arises (see [0004] in Patent Document 1). Thus, in the case of the oil layer/aqueous layer type, in view of the problem of obtaining a hair cosmetic which is "suitably emulsifiable and easily separable", it is necessary to select a suitable emulsifier.

Meanwhile, in the case of the emulsion layer/aqueous layer type of 2), similar to the case of the above oil layer/aqueous layer type, a hair cosmetic must be shaken to mix the two layers homogeneously immediately before use, the homogeneous state must be maintained during application to the hair, and the two layers must be separated again after a while. However, since the upper layer has to be restored as an emulsion layer, optimization of temporal stability of the emulsion layer (see [0020] of Patent Document 3), as well as of the duration required for separation is necessary (see [0008] to [0009] of the same document). Moreover, in the processes of emulsification and separation of the oil layer/aqueous layer type, the "emulsion particles", which are temporarily formed by shaking, gradually combine to form a large mass as time passes, and finally completely separated two layers are formed. In contrast, in the case of the emulsion layer/aqueous layer type, the "emulsion particles" are always present in the same condition and in the same particle size when homogeneously dispersed and when separated, and the "emulsion particles" (oily substance), having lower specific gravity than that of water, are gradually floated up and "volume of the lower layer (aqueous layer)" is changed, resulting to the separation of layers (see [0025] of Patent Document 4). Thus, the separation mechanisms of these two types are clearly different.

Furthermore, in the case of the emulsion layer/aqueous layer type, there is a unique problem where the aqueous layer sometimes becomes cloudy according to conditions even after the separation into two layers, which looks as if non-separated despite that they are separated, and thus, beautiful appearance cannot be obtained.

While, an emulsion layer/aqueous layer type cosmetic wherein a water-soluble polymer is incorporated for agglomeration of the particles in the clouding layer and for stabilizing them for a long duration has been reported (see Claim 1 and [0011] of Patent Document 5). The water-soluble polymer includes anionic and nonionic polymers, an anionic polymer is preferable, however specific compounds of the cationic polymer are not disclosed (see [0012] and Claim 3). Also, this cosmetic is intended to be used as a skin cosmetic, and there is no reference for using as a hair cosmetic.

Thus, there is no report for the two-layer separated type hair cosmetics (emulsion layer/aqueous layer type) satisfying the basic performances of hair cosmetics, such as temporal stability of the emulsion layer, appropriate separation rate (ordinarily, not greater than 24 hours, in view that a hair cosmetic is used at least once a day), beautiful appearance, and protection of hair and improvement of feel for touch.

PRIOR ART DOCUMENT

Patent Document

Patent Document 1: JP-A-H11-335237
Patent Document 2: JP-A-H11-222415
Patent Document 3: JP-A-H10-316539
Patent Document 4: JP-A-2002-003339
Patent Document 5: JP-A-2001-213720

SUMMARY OF THE INVENTION

The present invention provides a non-aerosol, two-layer separate type hair cosmetic composition which contains components (A) and (B) at a mass ratio (A)/(B) of from 0.2 to 10:

(A) from 0.1 to 6 mass % of a silicone selected from the group consisting of dimethicone, dimethiconol, and amino-modified silicone, wherein a number average degree of polymerization is from 300 to 20,000 and a number average particle diameter is from 0.05 to 20 μm, (B) a water-soluble cationic polymer with a weight-average molecular weight of from 50,000 to 1,000,000, selected from the group consisting of polyquaternium-6, polyquaternium-7, polyquaternium-16, and polyquaternium-22, and the composition consists of an oil-in-water emulsion layer and an aqueous layer.

DETAILED DESCRIPTION OF THE INVENTION

The present invention relates to a non-aerosol hair cosmetic composition having separated two layers of emulsion layer/aqueous layer, which satisfies basic performances as a hair cosmetic, such as temporal stability of the emulsion layer, appropriate rate of separation, beautiful appearance, manageability after the application, smoothness, combability, and non-stickiness.

The present inventors have found that the above problem can be solved by the incorporation of a silicone having a specific particle diameter and degree of polymerization, and a specific water-soluble cationic polymer at a specific ratio.

[(A): Silicone]

The silicone as component (A) has a number-average degree of polymerization of from 300 to 20,000 and is selected from the group consisting of dimethicone (dimethylpolysiloxane), dimethiconol (dimethylpolysiloxane having a hydroxy terminal group), and an amino-modified silicone.

A more preferable number-average degree of polymerization of silicone is, from the viewpoint of satisfying manageability, smoothness, and non-stickiness of hair after the hair cosmetic composition of the present invention is applied to the hair, from 1,000 to 15,000, preferably from 2,000 to 10,000 in the case of dimethicone, from 1,000 to 15,000, preferably from 2,000 to 10,000 in the case of dimethiconol, and from 300 to 10,000, preferably from 400 to 2,500 in the case of an amino-modified silicone.

The silicone as component (A) should have, from the viewpoints of making the rate of separation into two layers after shaking appropriate and the temporal stability of an oil-in-water emulsion layer, a particle diameter, as a number-average particle diameter, of from 0.05 to 20 μm, and even when the emulsion is separated into two layers, the particle diameter remains unchanged in the secondary agglomerates (described later in detail) formed by the action of a cationic polymer as component (B). The more preferable range of the average diameter is from 0.1 to 10 μm, more preferably from 0.3 to 5 μm. In the present specification, the particle diameter of the emulsion particle of component (A) is measured by using the laser diffraction/scattering particle size distribution measuring apparatus LA-910, product of Horiba Ltd., in which a sample diluted and circulated in purified water is measured in a batch cell.

The silicone as component (A) having a particle diameter in the above range may be prepared by forming an oil-in-water type emulsion using a common method, also a commercial product which has already been emulsified in advance may be used from the viewpoint of simplification of the production. Specific examples of such commercial products include BY22-029 (product of Dow Corning Toray, Co., Ltd.; nonionic emulsion of dimethicone oil), BY22-060 (product of Dow Corning Toray, Co., Ltd.; cationic emulsion containing a solution obtained by diluting highly polymerized dimethicone with a low viscosity silicone), BY22-019 (product of Dow Corning Toray, Co., Ltd.; nonionic and cationic emulsion containing a solution obtained by diluting highly polymerized dimethicone with cyclic silicone), BY22-020 (product of Dow Corning Toray, Co., Ltd.; cationic emulsion containing a solution obtained by diluting a highly polymerized dimethicone with light liquid isoparaffin), KM902 (product of Shin-Etsu Chemical Co., Ltd.; nonionic emulsion of highly polymerized dimethicone), KM903 (product of Shin-Etsu Chemical Co., Ltd.; cationic emulsion containing a solution obtained by diluting a highly polymerized dimethicone with a low viscosity silicone), X-52-2127 (product of Shin-Etsu Chemical Co., Ltd.; cationic emulsion containing a solution obtained by diluting a highly polymerized dimethicone with low viscosity silicone), X-52-2162 (product of Shin-Etsu Chemical Co., Ltd.; nonionic emulsion containing a solution obtained by diluting a highly polymerized dimethicone with low viscosity silicone), EMU101 (product of Momentive Performance Materials, Inc.; nonionic emulsion containing a solution obtained by diluting highly polymerized dimethicone with low viscosity silicone), XS65-B3803 (product of Momentive Performance Materials, Inc.; nonionic emulsion containing a solution obtained by diluting highly polymerized dimethicone with low viscosity silicone), DC 7-3100 (product of Dow Corning Toray Silicone, Co., Ltd.; nonionic emulsion containing a solution obtained by diluting dimethiconol with cyclic silicone), SM8704 Cosmetic Emulsion, SM8904 Cosmetic Emulsion (product of Dow Corning Toray, Co., Ltd.; cationic emulsion of amino-modified silicone), FZ-4672 (product of Dow Corning Toray, Co., Ltd.; nonionic emulsion of amino-modified silicone), and X-52-2265 (product of Shin-Etsu Chemical Co., Ltd.; nonionic emulsion of amino-modified silicone).

The amount of component (A) is from 0.1 to 6 mass %, preferably from 0.5 to 4 mass %, more preferably from 1 to 3 mass %, from the viewpoints of securing the apparent amount of the oil-in-water emulsion layer, and fulfilling manageability, smoothness, and non-stickiness of the hair after applying the hair cosmetic to the hair, as well as optimization of the rate of separation into two layers after shaking.

[(B): Water-Soluble Cationic Polymer]

The water-soluble cationic polymer as component (B) has a role of promoting the separation into the two layers, i.e., an oil-in-water emulsion layer and an aqueous layer, during standing still, by agglomeration of the oil-in-water emulsion particles of the silicone of component (A) to form large secondary agglomerates, however, unlike the case of an oil layer/aqueous layer type, the oil-in-water emulsion particles of component (A) are not combined to each other, and the particle diameter of component (A) itself is not changed. The component (B) is selected from polyquaternium-6 (dimethyldiallylammonium chloride polymer), polyquaternium-7 (dimethyldiallylammonium chloride/acrylamide copolymer), polyquaternium-16 (vinylimidazolinium trichloride/vinyl pyrrolidone copolymer), and polyquaternium-22 (dimethyldiallylammonium chloride/acrylic acid copolymer).

The component (B) should have a weight-average molecular weight of from 50,000 to 1,000,000, preferably from 100,000 to 900,000, more preferably from 120,000 to 500,000, from the viewpoint of obtaining an appropriate rate of separation into two layers after shaking and a transparency of the aqueous layer.

Examples of the commercial products of component (B) include Merquat 100 (product of NALCO Company; the number-average degree of polymerization is 150,000) as polyquaternium-6; Merquat 740 (product of NALCO COMPANY; the number-average degree of polymerization is 120,000) and Merquat 2200 (product of NALCO Company; the number-average degree of polymerization is 900,000) as polyquaternium-7; Luviquat FC370 (product of BASF SE; the number-average degree of polymerization is 100,000) and Luviquat FC550 (product of BASF SE; the number average degree of polymerization is 80,000) as polyquaternium-16, and Merquat 280 (product of NALCO Company; the number-average degree of polymerization is 450,000) and Merquat 295 (product of NALCO Company; the number-average degree of polymerization is 190,000) as polyquaternium-22.

The mass ratio (A)/(B) of components (A) and (B) should be from 0.2 to 10, preferably from 0.5 to 8, more preferably from 1 to 5, from the viewpoint of obtaining proper separation rate and transparency of the aqueous layer.

Although the content of component (B) is determined based on the mass ratio (A)/(B) from the viewpoint of obtaining proper separation rate and transparency of the aqueous layer, it is preferably from 0.05 to 2 mass %, more preferably from 0.1 to 1.5 mass %, and even more preferably from 0.2 to 1 mass % in the hair cosmetic composition of the present invention, from the viewpoint of eliminating stickiness from the hair cosmetic composition of the present invention.

[(C): Organic Carboxylic Acid or a Salt Thereof]

In the hair cosmetic composition of the present invention, from the viewpoint of contributing to the formation of the secondary agglomerates of components (A) and (B) by properly suppressing the enlargement of the polymer chain of component (B) in order to obtain appropriate rate of separation into two layers after shaking, further incorporation of an organic carboxylic acid or a salt thereof as component (C) is preferable. The examples of the organic carboxylic acid include hydroxy carboxylic acids, dicarboxylic acids, tricarboxylic acids, and acidic amino acids. More specifically, the hydroxy carboxylic acids include glycolic acid, lactic acid, malic acid, tartaric acid, and citric acid, the dicarboxylic acids include malonic acid, succinic acid, glutaric acid, adipic acid, maleic acid, fumaric acid, phthalic acid, and oxalic acid, the tricarboxylic acids include citric acid, and the acidic amino acids include glutamic acid and aspartic acid. Among these, malic acid, tartaric acid, malonic acid, succinic acid, maleic acid, lactic acid, citric acid, and glycolic acid are preferable, with malic acid, lactic acid, citric acid, and glycolic acid being more preferable. Examples of the salt of these organic carboxylic acids include salts with alkali metals, alkaline earth metals, ammonium, and organic amine compounds.

It is preferable to incorporate the organic carboxylic acid or a salt thereof in the hair cosmetic composition of the present invention at from 0.05 to 5 mass %, more preferably from 0.1 to 4 mass %, even more preferably from 1 to 3 mass %.

[(D): Organic Solvent]

From the viewpoint of obtaining an effect for reforming inner portion of the hair (the hollow repairing, etc.) and an effect for improvement of manageability, further incorporation of an organic solvent having a C log P of from −2 to 3 selected from the group consisting of aromatic alcohol, N-alkylpyrrolidone, alkylene carbonate, polypropylene glycol, lactone and cyclic ketone, as component (D), into the hair cosmetic composition of the present invention is preferable.

Examples of the organic solvent as component (D) include the following (D1) to (D5):

(D1) an aromatic alcohol represented by the general formula (1):

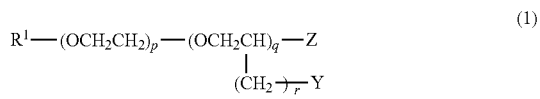

wherein $R^1$ represents a group $R^2$-Ph-$R^3$— ($R^2$ is a hydrogen atom, methyl group or methoxy group, $R^3$ is a bond or a saturated or unsaturated, divalent hydrocarbon group having 1 to 3 carbon atoms, and Ph is paraphenylene group), Y and Z represent a hydrogen atom or a hydroxyl group, and p, q and r stand for an integer of 0 to 5, with the proviso that when $p=q=0$, Z is not a hydrogen atom, and $R^1$ is not a group $R^2$-Ph- (D2) N-alkylpyrrolidone wherein an alkyl group having 1 to 18 carbon atoms is bound to the nitrogen atom (D3) an alkylene carbonate having 3 to 4 carbon atoms (D4) a polypropylene glycol with a number-average molecular weight of from 100 to 1,000

(D5) a lactone or a cyclic ketone represented by general formula (2), (3) or (4):

wherein X represents a methylene group or an oxygen atom, $R^4$ and $R^5$ represent substituents different from each other, and s and t stand for 0 or 1.

Of the organic solvents as component (D), examples of (D1) include benzyl alcohol, cinnamyl alcohol, phenethyl alcohol, p-anisyl alcohol, p-methyl benzyl alcohol, phenoxy ethanol, and 2-benzyloxyethanol. Examples of (D2) include N-methylpyrrolidone, N-octylpyrrolidone, and N-laurylpyrrolidone. Examples of (D3) include ethylene carbonate and propylene carbonate. The polypropylene glycol with a number-average molecular weight of from 100 to 1,000 as (D4) is preferably those having a number-average molecular weight of from 100 to 500, more preferably those having a degree of polymerization of from 2 to 5. In (D5), $R^4$ and $R^5$ of the general formulas (2) to (4) are preferably a linear, branched, or cyclic alkyl group, a hydroxyl group, a sulfonate group, a phosphate group, a carboxy group, a phenyl group, a sulfoalkyl group, a phosphoric acid alkyl group, a carboxyalkyl group, etc., more preferably a linear or branched alkyl group having 1 to 6 carbon atoms, such as a methyl group, an ethyl group, a propyl group, an isopropyl group, a butyl group, etc., which is a substitutent at γ-position in γ-lactone or δ-position in δ-lactone (i.e. the methylene group adjacent to the hetero oxygen atom). If the water solubility of compounds (2) to (4) is required to be increased, $R^4$ or $R^5$ is preferably an acidic group, such as a sulfonate group, a phosphate group, a carboxy group, etc., or an alkyl group substituted thereby. Examples of the lactone of (D5) include γ-butyrolactone, γ-caprolactone, γ-valerolactone, δ-valerolactone, δ-caprolactone, δ-heptanolactone, etc., but in terms of stability of lactone, γ-lactone, specifically γ-butyrolactone and γ-caprolactone are preferable.

Examples of the cyclic ketone of (D5) include cyclopentanone, cyclohexanone, cycloheptanone, and 4-methylcycloheptanone.

Examples of preferable component (D) include benzyl alcohol, 2-benzyloxyethanol, propylene carbonate and polypropylene glycol (having a number average molecular weight of from 300 to 500, preferably 400).

The component (D) used in the present invention is preferably liquid form at 25° C., and has a C log P of preferably from −2 to 3, more preferably from −1 to 2 in terms of promotion of permeation. A C log P is a calculated value of octanol-water-distribution coefficient (log P) defined by the formula below, which represents a distribution of a substance between an octanol phase and an aqueous phase, and the examples are described in Chemical Reviews, Vol. 71, 6 (1971).

$$\log P = \log([\text{Substance}]_{Octanol}/[\text{Substance}]_{Water})$$

wherein [Substance]$_{Octanol}$ represents a molar concentration of the substance in a 1-octanol phase, and [Substance]$_{Water}$ represents a molar concentration of the substance in an aqueous phase.

Specific examples of C log P of major components (D) include: benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64).

Two or more kinds of components (D) may be used in combination, and the content thereof is preferably from 0.01 to 5 mass %, more preferably from 0.05 to 3 mass %, even more preferably from 0.1 to 2 mass % in the hair cosmetic composition of the present invention.

[Ethanol]

The hair cosmetic composition of the present invention may further contain ethanol from the viewpoint of adjusting the specific gravity of the aqueous layer in order to regulate the rate of separation into two layers after shaking. The content of ethanol is preferably from 1 to 25 mass %, more preferably from 5 to 20 mass %, and even more preferably from 8 to 15 mass % in the hair cosmetic composition of the present invention, from the viewpoints of adjusting the rate of separation and preventing destruction of the oil-in-water emulsion particles of component (A).

[Surfactant]

The hair cosmetic composition of the present invention may contain a surfactant from the viewpoints of solubilization of a solvent, stability of the system, including dispersibility, etc., and enhancement of feel for touch. As the surfactant, any kinds of cationic surfactants, nonionic surfactants, amphoteric surfactants, and anionic surfactants may be used.

The cationic surfactant may be a quaternary ammonium salt represented by the following general formula (5):

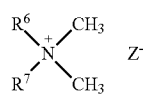

(5)

wherein $R^6$ and $R^7$ each independently represent a hydrogen atom, an alkyl group having 1 to 28 carbon atoms, or a benzyl group, with the proviso that $R^6$ and $R^7$ are not a hydrogen atom or a benzyl group, a lower alkyl group having 1 to 3 carbon atoms at the same time; and $Z^-$ stands for an anion.

Of $R^6$ and $R^7$, one is preferably an alkyl group having 16 to 24 carbon atoms, more preferably 16 to 18 carbon atoms, and even more preferably a linear alkyl group, and the other is preferably a lower alkyl group having 1 to 3 carbon atoms, more preferably a methyl group. Examples of the anion $Z^-$ include halide ions, such as a chloride ion and a bromide ion; and organic anions, such as an ethylsulfuric acid ion and a methyl carbonate ion; among these, a halide ion, specifically a chloride ion, is preferable.

The cationic surfactant is preferably a mono long-chain alkyl quaternized ammonium salt, specific examples of which include cetyltrimethylammonium chloride, stearyltrimethylammonium chloride, arachyltrimethylammonium chloride, and behenyltrimethylammonium chloride; among these, stearyltrimethylammonium chloride and cetyltrimethylammonium chloride are preferable.

Examples of the nonionic surfactants include polyoxyalkylene alkyl ether, polyoxyalkylene alkenyl ether, higher fatty acid sucrose ester, polyglycerine fatty acid ester, higher fatty acid mono- or diethanol amide, polyoxyethylene hardened castor oil, polyoxyethylene sorbitan fatty acid ester, polyoxyethylene sorbitol fatty acid ester, alkylsaccharide surfactants, alkyl amine oxide, and alkylamidoamine oxide; among these, polyoxyalkylene alkyl ether and polyoxyethylene hardened castor oil, specifically polyoxyethylene alkyl ether, are preferable.

Examples of the amphoteric surfactants include imidazoline, carbobetaine, amidobetaine, sulfobetaine, hydroxysulfobetaine, and amidosulfobetaine surfactants.

Examples of the anionic surfactants include an alkyl benzene sulfonate salt, alkyl or alkenyl ether sulfate salt, alkyl or alkenyl sulfate salt, olefin sulfonate salt, alkane sulfonate salt, saturated or unsaturated fatty acid salt, alkyl or alkenyl ether carboxylate salt, α-sulfone fatty acid salt, N-acylamino acid surfactant, phosphoric acid mono or diester surfactant, and sulfosuccinic acid ester.

Examples of the counterion of the anionic residue of the surfactant include alkali metal ions, such as a sodium ion and a potassium ion; alkaline earth metal ions, such as a calcium ion and a magnesium ion; an ammonium ion; and an alkanolamine having 1 to 3 alkanol groups having 2 or 3 carbon atoms (for example, monoethanolamine, diethanolamine, triethanolamine, triisopropanolamine, etc.).

Examples of the counterion of the cationic residue of the surfactant include a halide ion, such as chloride ion, bromide ion, and iodide ion; methosulfate ion; and saccharinate ion.

Of these, in view of feel for touch as a hair cosmetic, a cationic surfactant is preferable. Surfactants may be used singly or in combination of 2 or more kinds, and in view of making the rate of separation into two layers after shaking appropriate, the content thereof is preferably from 0.01 to 5 mass %, more preferably from 0.02 to 2 mass %, and even more preferably from 0.05 to 1 mass %, in the hair cosmetic composition of the present invention.

[Poly(N-acylalkyleneimine)-Modified Silicone]

The hair cosmetic composition of the present invention may further contain poly(N-acylalkyleneimine)-modified silicone from the viewpoint of natural manageability of the hair. The poly(N-acylalkyleneimine)-modified silicone may have a poly(N-acylalkyleneimine) segment containing the repeating unit represented by the following general formula (6):

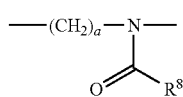

(6)

(wherein $R^8$ represents a hydrogen atom, an alkyl group having 1 to 22 carbon atoms, a cycloalkyl group, an aralkyl group or an aryl group, and a stands for a number of 2 or 3), and an organopolysiloxane segment, and the two segments combine with each other via a heteroatom-containing alkylene group bound to at least one of the silicon atoms of the organopolysiloxane segment. The alkyl group represented by $R^8$ is preferably a group having 1 to 20 carbon atoms, more preferably 1 to 5 carbon atoms, and even more preferably 1 or 2 carbon atoms. The cycloalkyl group may be a group having 3 to 6 carbon atoms, the aralkyl group may be phenylalkyl, naphthylalkyl, etc., the aryl group may be phenyl, naphthyl, alkyl-substituted phenyl, etc.; and $R^8$ is preferably a methyl group or an ethyl group.

A mass ratio of organopolysiloxane segment/poly(N-acylalkyleneimine) segment of the poly(N-acylalkyleneimine)-modified silicone is preferably from 98/2 to 40/60, more preferably from 95/5 to 65/35, and even more preferably from 90/10 to 68/32. The mass-average molecular weight thereof is preferably from 40,000 to 500,000, more preferably from 42,000 to 300,000, and even more preferably from 44,000 to 200,000.

Examples of the heteroatom-containing alkylene group connecting the organopolysiloxane segment and the poly(N-acylalkyleneimine) segment include an alkylene group having 2 to 20 carbon atoms and containing 1 to 3 nitrogen atoms, oxygen atoms, and/or sulfur atoms. Specific examples thereof include:

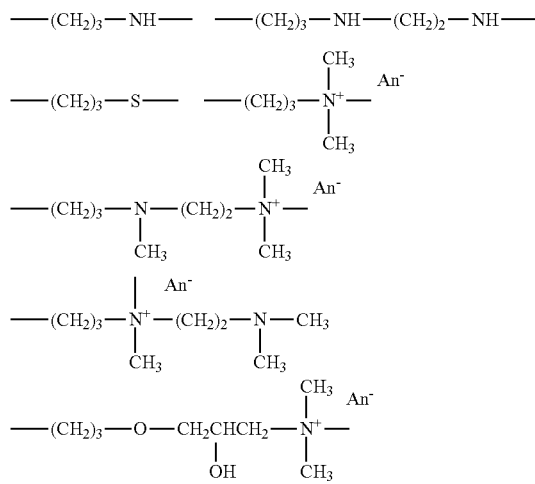

wherein $An^-$ represents an anion. Among these, an alkylene group having 2 to 5 carbon atoms which contains a nitrogen atom is preferable.

The poly(N-acylalkyleneimine)-modified silicone can be produced, for example, by the process described in JP-A-H07-133352.

Examples of the poly(N-acylalkyleneimine)-modified silicone include polysilicone-9, such as poly(N-formylethyleneimine)organosiloxane, poly(N-acetylethyleneimine)organosiloxane, and poly(N-propionylethyleneimine)organosiloxane.

The content of the poly(N-acylalkyleneimine)-modified silicone is preferably from 0.01 to 10 mass %, more preferably from 0.05 to 5 mass %, and even more preferably from 0.1 to 2 mass %, in the hair cosmetic composition of the present invention.

[Polyol]

The hair cosmetic composition of the present invention may contain a polyol from the viewpoints of permeation of each component of the hair cosmetic composition of the present invention into the hair and the improvement of feel for touch. Examples of the polyol include ethylene glycol, glycerine, sorbitol, propylene glycol, 1,3-butylene glycol, and dipropylene glycol, with glycerine, propylene glycol, 1,3-butylene glycol, and dipropylene glycol being preferable. The polyol may be used singly or in combination of two or more, and its content is preferably from 0.1 to 10 mass %, more preferably from 0.5 to 7 mass %, and even more preferably from 1 to 5 mass %, in the hair cosmetic composition of the present invention.

[pH]

In the hair cosmetic composition of the present invention, from the viewpoint of obtaining the appropriate rate of separation into two layers after shaking by suppressing the expansion of the polymer chain of component (B) and contributing to the formation of secondary agglomerates of components (A) and (B), it is preferable to adjust the pH at 25° C. from 2 to 6.5, more preferably pH from 2.5 to 5.5, and even more preferably pH from 3 to 4.5. To adjust the pH to fall within the above range, inorganic acids, such as hydrochloric acid, sulfuric acid, and phosphoric acid, and alkaline agents, such as sodium hydroxide and potassium hydroxide, may be used in addition to the above-described organic carboxylic acids.

[Viscosity]

In the hair cosmetic composition of the present invention, from the viewpoint of making the rate of separation into two layers after shaking appropriate, the viscosity in a homogeneously mixed condition is preferably not greater than 300 mPa·s, more preferably not greater than 100 mPa·s, and even more preferably not greater than 50 mPa·s. A lower limit is not particularly specified, but is preferably not lower than 0.5 mPa·s, more preferably not lower than 0.7 mPa·s, and even more preferably not lower than 1 mPa·s. The viscosity herein is a value obtained after the rotation at 25° C. for 1 minute at 60 rpm, using in combination, a rotor No.M2 when measuring a viscosity of not lower than 80 mPa·s and not greater than 300 mPa·s; a rotor No.M1 when measuring a viscosity of not lower than 15 mPa·s and lower than 80 mPa·s; or an L-adaptor when measuring a viscosity of lower than 15 mPa·s. The rotors are used sequentially from the rotor for measuring a low viscosity, the measurement is completed when the measurement can be performed within the measuring limit, and thereafter no measurement using another rotor is performed. The measurement is performed immediately after homogeneously mixing the hair cosmetic at 25° C., in a constant-temperature bath of 25° C.

[Water]

The hair cosmetic composition of the present invention may contain water as a solvent.

[Others]

The hair cosmetic composition of the present invention may contain, in addition to the above components, the other components used in ordinary hair cosmetics according to use as needed. Examples of such components include antidandruff agents; vitamins; bactericides; anti-inflammatory agents; antiseptics; chelating agents; humectants, such as panthenol; coloring agents, such as dyes and pigments; plant extracts; pearlescent agents; fragrances; ultra-violet ray absorbers; anti-oxidants; and other components as recited in the "ENCYCLOPEDIA OF SHAMPOO INGREDIENTS (MICELLE PRESS)".

The hair cosmetic composition of the present invention is preferably used as a hair conditioning agent, a hair styling agent, etc. A container for holding the hair cosmetic is a non-aerosol container, such as a shaking-out container, a pump dispenser, a pump spray, a pump foamer, and a squeeze foamer. Since, unlike an aerosol type container, a non-aerosol type container does not need a propellant, there is no breakdown of the oil-in-water emulsion particles of component (A) due to the propellant.

[Method of Use]

The hair cosmetic composition of the present invention is well shaken before use and used either by directly spraying it to the hair before it starts to separate into the oil-in-water emulsion layer and the aqueous layer, or by dropping it on the palm, extending it by the palms, and applying it to the hair. After the application, by heating or natural drying, component (A) can be extended on the surface of the hair, and the permeation of various components into the hair can be promoted.

EXAMPLES

Examples 1 to 8 and Comparative Examples 1 to 8

Two-layer separate type hair cosmetic compositions shown in Table 1 were prepared and evaluated with regard to the "rate of separation into two layers", "turbidity of the lower layer", "temporal stability", and "performance as a hair cosmetic", in accordance with the following methods and criteria.

"Rate of Separation into Two Layers"

A colorless, transparent, cylindrical PET container having an inner diameter of about 3 cm and a height of about 12 cm was filled with a homogeneously mixed two-layer separate type hair cosmetic at 25° C. until the height of the hair cosmetic from the bottom becomes 10 cm. After filling the liquid, the PET container was left standing at an atmosphere of 25° C., and the interface between the upper layer and the lower layer after a certain time has passed was visually observed.

A: After 24 hours, the interface was observed at a position of not lower than 4 cm from the bottom B: After 24 hours, the interface was observed at a position of lower than 4 cm from the bottom C: No interface was observed after 24 hours "Turbidity of the Lower Layer"

Using Turbiscan MA2000 (product of Formulaction SA), the intensity of the transmitted light through the lower layer after being left standing for 24 hours was measured under the following conditions:

◆Light source: LED pulse light (850 nm), ◆Scan interval (resolution): 40 μm, ◆Optical path length: 16 mm, ◆Amount of sample: 7.0 g, ◆Temperature of sample: 30° C.

A: Transmittance of the lower layer was 75 to 100%

C: The upper layer was not separated from the lower layer, or the transmittance of the lower layer was lower than 75%

"Temporal Stability"

After the hair cosmetic composition was preserved for 1 month at 50° C., the change in appearance of the solution was visually evaluated. A solution not changed from the initial state was evaluated as "A", a solution slightly changed was evaluated as "B", and a solution changed (changed into translucent or transparent in the turbid upper layer) was evaluated as "C".

"Performance as a Hair Cosmetic"

10 expert panelists used the hair cosmetic compositions and carried out 4-stage sensory evaluation, as to manageability, smoothness and combability immediately after use, and absence of stickiness of the hair when used and after used, according to the following criteria:

4 points: good, 3 points: somewhat good, 2 points: not very good, and 1 point: bad The evaluation result was obtained by summing up the points of the 10 panelists, according to the following criteria.

A: 33 to 40 points
AB: 25 to 32 points
B: 17 to 24 points
C: 10 to 16 points

TABLE 1

| (Mass %; Each content is an active amount) | Example 1 | 2 | 3 | 4 | 5 | 6 | 7 | 8 |
|---|---|---|---|---|---|---|---|---|
| Dimethicone emulsion (X-52-2162, Shin-Etsu Chemical) Particle diameter: 1 μm | 1.8 | — | 0.5 | 1.8 | 1.8 | 1.8 | 0.3 | 3.5 |
| Amino-modified silicone emulsion (SM8704 Cosmetic Emulsion, Dow Corning Toray) Particle diameter: 0.08 μm | — | 1.2 | — | — | — | — | — | — |
| Dimethicone emulsion (Silicone CF2460, Dow Corning Toray) Particle diameter 50 μm | — | — | — | — | — | — | — | — |
| Polyquaternium-6 (Merquat 100, NALCO) Weight-average molecular weight: 150,000 | 0.5 | 0.5 | 0.4 | — | — | — | 0.7 | 0.4 |
| Polyquaternium-22 (Merquat 280, NALCO) Weight-average molecular weight: 450,000 | — | — | — | 0.8 | — | — | — | — |
| Polyquaternium-7 (Merquat 2200, NALCO) Weight-average molecular weight: 900,000 | — | — | — | — | 0.4 | — | — | — |
| Polyquaternium-16 (LuviquatFC370, BASF) Weight-average molecular weight: 100,000 | — | — | — | — | — | 0.8 | — | — |
| Polyquaternium-7 (Merquat 550, NALCO) Weight-average molecular weight: 1,600,000 | — | — | — | — | — | — | — | — |
| Polyquaternium-16 (Luviquat Excellence, BASF) Weight-average molecular weight: 40,000 | — | — | — | — | — | — | — | — |
| Polyquaternium-10 (Caticello M-80, Kao) Weight-average molecular weight: 800,000 | — | — | — | — | — | — | — | — |
| Ethanol | 12.0 | 12.0 | 12.0 | 12.0 | 12.0 | 12.0 | 12.0 | 12.0 |
| Glycerol | 2.0 | 2.0 | 2.0 | 2.0 | 2.0 | 2.0 | 2.0 | 2.0 |
| Dipropylene glycol | 2.0 | 2.0 | 2.0 | 2.0 | 2.0 | 2.0 | 2.0 | 2.0 |
| Benzyl alcohol | 0.2 | 0.2 | 0.2 | 0.2 | 0.2 | 0.2 | 0.2 | 0.2 |
| Trideceth-9 | 0.5 | 0.5 | 0.5 | 0.5 | 0.5 | 0.5 | 0.5 | 0.5 |
| Cetrimonium chloride (Quartamin 60W, Kao) | 0.2 | 0.2 | 0.2 | 0.2 | 0.2 | 0.2 | 0.2 | 0.2 |
| Lactic acid | 0.9 | 0.9 | 0.9 | 0.9 | 0.9 | 0.9 | 0.9 | 0.9 |
| Malic acid | 0.9 | 0.9 | 0.9 | 0.9 | 0.9 | 0.9 | 0.9 | 0.9 |
| Polysilicone-9 (Elastomer OS-88, KAO) | 0.2 | 0.2 | 0.2 | 0.2 | 0.2 | 0.2 | 0.2 | 0.2 |
| Sodium hydroxide | * | * | * | * | * | * | * | * |
| Water | Balance | Balance | Balance | Balance | Balance | Balance | Balance | Balance |

TABLE 1-continued

| (Mass %; Each content is an active amount) | | | | | | | | |
|---|---|---|---|---|---|---|---|---|
| (A)/(B) mass ratio | 3.6 | 2.4 | 1.3 | 4.5 | 4.5 | 2.3 | 0.4 | 8.8 |
| Rate of separation into milk white layer/transparent layer | A | A | A | A | A | A | A | A |
| Turbidity of the lower layer | A | A | A | A | A | A | A | A |
| Temporal stability | A | A | A | A | A | A | A | A |
| Manageability of the hair | A | A | AB | A | A | A | AB | A |
| Smoothness of the hair | A | A | A | A | A | A | AB | A |
| Combability of the hair | A | A | AB | A | A | A | AB | A |
| Absence of stickiness of the hair | A | A | A | A | A | AB | A | AB |

| (Mass %; Each content is an active amount) | Comparative Example | | | | | | | |
|---|---|---|---|---|---|---|---|---|
| | 1 | 2 | 3 | 4 | 5 | 6 | 7 | 8 |
| Dimethicone emulsion (X-52-2162, Shin-Etsu Chemical) Particle diameter: 1 μm | 1.8 | 7.0 | — | 1.8 | 1.8 | 1.8 | 0.1 | 5.0 |
| Amino-modified silicone emulsion (SM8704 Cosmetic Emulsion, Dow Corning Toray) Particle diameter: 0.08 μm | — | — | — | — | — | — | — | — |
| Dimethicone emulsion (Silicone CF2460, Dow Corning Toray) Particle diameter 50 μm | — | — | 1.8 | — | — | — | — | — |
| Polyquaternium-6 (Merquat 100, NALCO) Weight-average molecular weight: 150,000 | — | 1.9 | 0.5 | — | — | — | 1.0 | 0.42 |
| Polyquaternium-22 (Merquat 280, NALCO) Weight-average molecular weight: 450,000 | — | — | — | — | — | — | — | — |
| Polyquaternium-7 (Merquat 2200, NALCO) Weight-average molecular weight: 900,000 | — | — | — | — | — | — | — | — |
| Polyquaternium-16 (LuviquatFC370, BASF) Weight-average molecular weight: 100,000 | — | — | — | — | — | — | — | — |
| Polyquaternium-7 (Merquat 550, NALCO) Weight-average molecular weight: 1,600,000 | — | — | — | 0.3 | — | — | — | — |
| Polyquaternium-16 (Luviquat Excellence, BASF) Weight-average molecular weight: 40,000 | — | — | — | — | 0.4 | — | — | — |
| Polyquaternium-10 (Caticello M-80, Kao) Weight-average molecular weight: 800,000 | — | — | — | — | — | 0.4 | — | — |
| Ethanol | 12.0 | 12.0 | 12.0 | 12.0 | 12.0 | 12.0 | 12.0 | 12.0 |
| Glycerol | 2.0 | 2.0 | 2.0 | 2.0 | 2.0 | 2.0 | 2.0 | 2.0 |
| Dipropylene glycol | 2.0 | 2.0 | 2.0 | 2.0 | 2.0 | 2.0 | 2.0 | 2.0 |
| Benzyl alcohol | 0.2 | 0.2 | 0.2 | 0.2 | 0.2 | 0.2 | 0.2 | 0.2 |
| Trideceth-9 | 0.5 | 0.5 | 0.5 | 0.5 | 0.5 | 0.5 | 0.5 | 0.5 |
| Cetrimonium chloride (Quartamin 60W, Kao) | 0.2 | 0.2 | 0.2 | 0.2 | 0.2 | 0.2 | 0.2 | 0.2 |
| Lactic acid | 0.9 | 0.9 | 0.9 | 0.9 | 0.9 | 0.9 | 0.9 | 0.9 |
| Malic acid | 0.9 | 0.9 | 0.9 | 0.9 | 0.9 | 0.9 | 0.9 | 0.9 |
| Polysilicone-9 (Elastomer OS-88, KAO) | 0.2 | 0.2 | 0.2 | 0.2 | 0.2 | 0.2 | 0.2 | 0.2 |
| Sodium hydroxide | * | * | * | * | * | * | * | * |
| Water | Balance | Balance | Balance | Balance | Balance | Balance | Balance | Balance |
| (A)/(B) mass ratio | — | 3.7 | 3.6 | 6.0 | 4.5 | 1.5 | 0.1 | 12.0 |
| Rate of separation into milk white layer/transparent layer | C | B | A | C | A | C | A | A |
| Turbidity of the lower layer | C | A | A | C | C | C | A | C |
| Temporal stability | B | A | C | B | A | A | A | B |
| Manageability of the hair | A | AB | A | A | A | A | C | AB |
| Smoothness of the hair | AB | B | AB | AB | A | B | C | B |
| Combability of the hair | A | C | AB | B | A | B | B | AB |
| Absence of stickiness of the hair | A | C | B | B | A | B | B | AB |

*: An amount for adjusting the pH to 3.7

Formulation Example 1

| | (mass %) |
|---|---|
| Water | balance |
| Dimethicone emulsion (X-52-2162, Shin-Etsu Chemical, particle diameter 1 μm) | 1.8 (active amount) |
| Polyquaternium-22 (Merquat 295, NALCO, weight-average molecular weight: 190,000) | 0.4 (active amount) |
| Ethanol | 14.0 |
| Trideceth-9 (Softanol 90, Nippon Shokubai) | 0.4 |
| Cetrimonium chloride (Quartamin 60W, Kao) | 0.24 (active amount) |
| Lactic acid | 0.1 |
| Sodium hydroxide | an amount for adjusting pH to 4.2 |

Formulation Example 2

| | (mass %) |
|---|---|
| Water | balance |
| Dimethicone emulsion (X-52-2162, Shin-Etsu Chemical, particle diameter 1 μm) | 1.8 (active amount) |
| Polyquaternium-7 (Merquat 2200, NALCO, weight-average molecular weight: 900,000) | 0.5 |
| Ethanol | 10.0 |
| Dipropylene glycol | 3.0 |
| Benzyl alcohol | 0.5 |
| Trideceth-9 (Softanol 90, Nippon Shokubai) | 0.4 |
| Cetrimonium chloride (Quartamin 60W, Kao) | 0.24 (active amount) |
| Lactic acid | 1.3 |
| Malic acid | 1.3 |

-continued

| | (mass %) |
|---|---|
| Sodium hydroxide | an amount for adjusting pH to 3.7 |

Formulation Example 3

| | (mass %) |
|---|---|
| Water | balance |
| Dimethiconol emulsion (Dow Corning 7-3100, Dow Corning, particle diameter: 1 μm) | 0.8 (active amount) |
| Polyquaternium-6 (Merquat 100, NALCO, weight-average molecular weight: 150,000) | 0.48 (active amount) |
| Ethanol | 12.0 |
| Glycerol | 1.0 |
| Dipropylene glycol | 2.5 |
| Benzyl alcohol | 0.3 |
| Trideceth-9 (Softanol 90, Nippon Shokubai) | 0.5 |
| Cetrimonium chloride (Quartamin 60W, Kao) | 0.24 (active amount) |
| Lactic acid | 0.6 |
| Malic acid | 0.6 |
| Polysilicone-9 (Elastomer OS-88, Kao) | 0.4 |
| Sodium hydroxide | an amount for adjusting pH to 3.7 |

Formulation Example 4

| | (mass %) |
|---|---|
| Water | balance |
| Dimethicone emulsion (BY22-060, Dow Corning Toray, particle diameter: 0.5 μm) | 0.97 (active amount) |
| Polyquaternium-6 (Merquat 100, NALCO, weight-average molecular weight: 150,000) | 0.48 (active amount) |
| Ethanol | 11.0 |
| Glycerol | 2.0 |
| Dipropylene glycol | 2.0 |
| Benzyl alcohol | 0.2 |
| Trideceth-9 (Softanol 90, Nippon Shokubai) | 0.5 |
| 30 mass % aqueous solution of cetrimonium chloride (Quartamin 60W, Kao) | 0.8 |
| Lactic acid | 0.6 |
| Malic acid | 0.6 |
| Polysilicone-9 (Elastomer OS-88, Kao) | 0.4 |
| Sodium hydroxide | an amount for adjusting pH to 3.7 |

The invention claimed is:

1. A non-aerosol hair cosmetic composition, comprising components (A), (B), (C), (D) (E), and (F), wherein components (A) and (B) at a mass ratio of (A)/(B) of from 0.2 to 10:
  (A) dimethicone with a number-average degree of polymerization of from 1,000 to 15,000 having a number-average particle diameter of from 0.05 to 20 μm and in an amount of from 0.1 to 6 mass %
  (B) from 0.05 to 2 mass % of a water-soluble cationic polymer with a weight-average molecular weight of from 120,000 to 500,000, selected from the group consisting of polyquaternium-6, polyquaternium-7, polyquaternium-16, and polyquaternium-22,
  (C) from 1 to 3 mass % of an organic carboxylic acid or a salt thereof,
  (D) from 0.01 to 5 mass % of an organic solvent selected from the group consisting of benzyl alcohol, cinnamyl alcohol, phenethyl alcohol, p-anisyl alcohol, p-methylbenzyl alcohol, phenoxyethanol, and 2-benzyloxyethanol
  (E) from 8 to 15 mass % of ethanol, and
  (F) from 0.01 to 5 mass % of a surfactant,
  wherein the composition consists of an oil-in-water emulsion layer comprising components (A) and (B) and an aqueous layer, and wherein the viscosity of said composition ranges from 0.5 mPa·s to 100 mPa·s, wherein said viscosity is determined after rotation at 25° C. for 1 minute at 60 rpm.

2. The non-aerosol hair cosmetic composition according to claim 1, having a pH of from 2 to 6.5.

3. The non-aerosol hair cosmetic composition according to claim 1, wherein the number average particle diameter of component (A) is from 0.1 to 10 μm.

4. The non-aerosol hair cosmetic composition according to claim 1, wherein component (C) is an organic carboxylic acid or a salt thereof, wherein said organic carboxylic acid is selected from the group consisting of glycolic acid, lactic acid, malic acid, tartaric acid, citric acid, malonic acid, succinic acid, and maleic acid.

5. The non-aerosol hair cosmetic composition according to claim 1, wherein (F) is from 0.02 to 2 mass % of a surfactant.

6. The non-aerosol hair cosmetic composition according to claim 1, wherein component (C) is an organic carboxylic acid or a salt thereof, wherein said organic carboxylic acid is selected from the group consisting of glycolic acid, lactic acid, malic acid, tartaric acid, citric acid, malonic acid, succinic acid, glutaric acid, adipic acid, maleic acid, fumaric acid, phthalic acid, oxalic acid, glutamic acid, and aspartic acid.

7. The non-aerosol hair cosmetic composition according to claim 1, wherein the viscosity of said composition is from 0.7 to 50 mPa·s, wherein said viscosity is determined after rotation at 25° C. for 1 minute at 60 rpm.

* * * * *